United States Patent [19]

Hardtmann et al.

[11] 4,451,464
[45] May 29, 1984

[54] TRIFLUOROMETHYL SUBSTITUTED TRICYCLIC QUINAZOLINONES USEFUL AS TRANQUILIZERS

[75] Inventors: Goetz E. Hardtmann, Morristown; William J. Houlihan, Mt. Lakes, both of N.J.

[73] Assignee: Sandoz, Inc., E. Hanover, N.J.

[21] Appl. No.: 427,282

[22] Filed: Sep. 29, 1982

Related U.S. Application Data

[63] Continuation-in-part of Ser. No. 401,649, Jul. 26, 1982, abandoned, which is a continuation of Ser. No. 302,486, Sep. 16, 1981, abandoned.

[51] Int. Cl.³ .................. A61K 31/505; C07D 487/04
[52] U.S. Cl. ..................................... 424/251; 544/250
[58] Field of Search ........................ 544/250; 424/251

[56] References Cited

U.S. PATENT DOCUMENTS 3,280,117 10/1966 Griot .............................. 544/250 X
3,598,823  8/1971 Hardtmann ...................... 544/250
3,621,025 11/1971 Jen et al. .......................... 544/250
3,963,720  6/1976 Hardtmann ...................... 544/247

Primary Examiner—Donald G. Daus
Assistant Examiner—D. Rivers
Attorney, Agent, or Firm—Gerald D. Sharkin; Richard E. Vila

[57] ABSTRACT

Tranquilizers are of the formula:

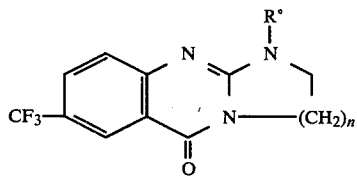

wherein
R° is alkyl of 1 to 8 carbon atoms, and
n is 1 or 2.

19 Claims, No Drawings

TRIFLUOROMETHYL SUBSTITUTED TRICYCLIC QUINAZOLINONES USEFUL AS TRANQUILIZERS

This is a continuation-in-part of application Ser. No. 401,649, filed July 26, 1982, which is a continuation of application Ser. No. 302,486 filed Sept. 16, 1981, now both abandoned.

The present invention relates to trifluoromethyl substituted tricyclic compounds which are quinazolinones, and also relates to methods and compositions for utilization of the compounds based on their biological activity.

The compounds of the invention may be represented for convenience of description by the following structural formula I:

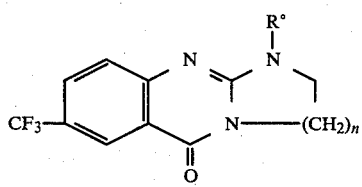

wherein
R° is alkyl of 1 to 8 carbon atoms, and
n is 1 or 2.

The compounds of the formula I may be prepared by reacting in a process (a) the compound of the formula II:

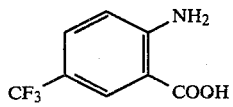

with a compound of the formula III:

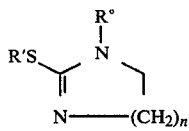

wherein R° and n are as defined and R' is alkyl of 1 to 4 carbon atoms or benzyl.

The preparation of compounds I by the reaction of compounds II and III may be suitably carried out at elevated temperatures typically in the range of from 100° C. to 190° C., preferably 140° C. to 180° C. The reaction is conveniently carried out in an inert organic solvent of conventional type, preferably a higher boiling organic solvent such as dimethylacetamide and dimethylformamide, more preferably dimethylacetamide. The reaction products of formula I may be recovered from the reaction mixture by working up by established procedures.

The compounds of the formula I may also be prepared by reacting in a process (b) the compound of the formula IV:

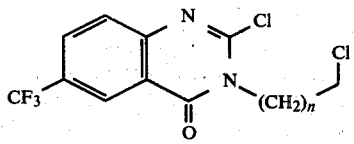

in which n is as defined, with a compound of the formula V:

$$R°-NH_2 \quad\quad V$$

wherein R° is as defined.

The preparation of the compounds of the formula I by reaction of compounds IV and V may be suitably carried out temperatures of from 20° C. to 160° C., preferably 40° C. to 90° C. The reaction is conveniently carried out in the presence of an inert organic solvent such as dimethylacetamide or a lower alkanol, eg. ethanol. The resulting reaction product of the formula I may be recovered from the resulting reaction mixture by working up by establishing procedures.

The compound of the formula IV may be conveniently prepared by thermal rearrangement of the compound of the formula VI:

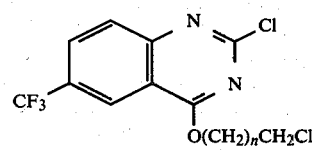

in which n is as defined.

Such preparation of the compound IV from the compound VI can be effected in the melt at temperatures of the order of about 200° C. ranging up to 300° C., preferably under reduced pressure conditions. The desired product of the formula IV is recoverable in refined form by established procedures such as crystallization of the solid resulting from cooling of the reaction system. The compounds of the formula IV can also be prepared by heating under reflux a compound of the formula VI in an inert solvent boiling at temperatures of at least about 200° C., eg. dichlorobenzene or trichlorobenzene, typically for a period of from 3 to 8 hours.

The compounds of the formulae II, III, V and VI employed as starting materials in the above-described processes are either known per se or may be prepared from known materials by procedures analogous to those used for the known compounds.

The compounds of the formula I may also be prepared by other procedures, in particular those basic procedures described in U.S. Pat. No. 3,598,823 wherein the 1-alkali metal salts of the route tricyclic compound (compounds I herein in which R° would be an alkali metal) by reaction thereof with an R°-halide as described in said patent, the necessary starting materials being known or readily preparable by known procedures.

The compounds of the formula I form acid addition salts which are included within the scope of the present invention. Those salts forming pharmaceutically acceptable salt forms, eg. the hydrochloride, may of course be used pharmaceutically in accordance with the invention. The acid addition salts may be produced from the corresponding free bases by conventional procedures. Conversely, the free bases may be obtained from the salts by procedures known in the art.

The compounds of the formula I exhibit a Central Nervous System depressant effect in mammals and are useful as tranquilizers as indicated by the Flunitrazepam Receptor Binding Assay in accordance with the method basically described by R. C. Speth et al., *Life Science,* 22:859 (1978), and by the conflict segment of the well known Geller Conflict test in rats (1-20 mg./kg.) as described by J. Geller, Psychopharmacologia, Vol. 1, pages 482-492 (1960).

Routine and non-substantive modifications of the Flunitrazepam Receptor Binding Assay (hereinafter FBA TEST No. 1) that are evident from the following description are employed in such evaluation in which non-radioactive candidate compounds are tested for their ability to displace $^3$H-flunitrazepam binding from isolated calf brain benzodiazepine receptors. Hence, an aliquot of frozen calf caudate tissue is thawed and diluted with 0.5 M Tris buffer containing metal ions (120 mM NaCl, 5 mM KCL, 2 mM $CaCl_2$ and 1 mM $MgCl_2$) to a final concentration of 8 mg/ml, i.e., a 25 fold dilution. This suspension is made homogenous by homogenation with a Brinkmann Polytron using a rheostat setting of 8 for 10 seconds. Ten λ of $^3$H-flunitrazepam solution is diluted in 0.05 M Tris buffer (pH 7.1 at 37° C.) to give a concentration of 10 nM ($3.13 \times 10^{-6}$ mg/ml). This solution is stored frozen at −20° C., while the stock $^3$H-flunitrazepam solution in ethanol is kept refrigerated at +2° C. Periodically, the stock ethanolic $^3$H-flunitrazepam solution is examined by TLC for chemical purity. If the purity becomes <90%, the stock solution is repurified or new high purity $^3$H-flunitrazepam is obtained and the impure $^3$H-flunitrazepam discarded. A 0.1 ml portion of 10 nM $^3$H-flunitrazepam "working" solution is added to 12×75 mm borosilicate disposable test tube along with 0.1 ml of freshly prepared 10% ethanol solution. This is the control tube for measuring total binding. Nonspecific binding is determined by the addition of $2 \times 10^{-5}$ M diazepam (in 10% ethanol) to other tubes in the place of 0.1 ml 10% ethanol. The specific binding is determined in the final results by subtraction of the non-specific binding from the total binding. All compounds screened have their results expressed in terms of specific binding and are tested at a final concentration of $1 \times 10^{-6}$ M. Three mg of each compound are placed in 18×150 mm borosilicate disposable test tubes. These tubes are kept in the dark at room temperature until the day of the assay at which time 10 ml of absolute ethanol is added and the tubes placed in a Branson Ultrasonic Cleaner for 15 minutes and then vortexed in order to put the compounds into solution. All tubes are closely examined to make certain the compound is completely in solution. If not, then 3 drops of 2 N HCl is added. If the compound is still not in solution but a cloudy homogenous suspension is found, then the subsequent serial dilutions are continued. This gives a concentration of $\sim 1 \times 10^{-3}$ M. The compounds are further diluted by serial dilution as follows: 0.1 ml of the $10^{-3}$ M solution is added to 0.9 ml of 100% ethanol and vortexed. A 0.1 ml portion of this solution is added to 0.9 ml of water to give $\sim 1 \times 10^{-5}$ M solution. A 0.1 ml portion of this soluion is added to 12×75 mm test tubes for assay. All assays are run in duplicate. A 0.8 ml portion of caudate tissue suspension is added to all tubes, vortexed, incubated at 2° C. for 120 minutes, and rapidly filtered under vacuum through Whatman GF/G glass fiber filters. Each tube is rinsed once with 3 ml ice-cold 50 mM Tris buffer (pH 7.1 at 37° C.) and the filter subsequently washed once with 6 ml of the same Tris buffer. The $^3$H-flunitrazepam trapped on the filters is counted by liquid scintillation counting on a Beckman LS 8000 after the filters are rapidly shaken for 45 minutes in the scintillation vials with 10 ml of scintillation cocktail. Results of compounds screened are calculated by the on-line data reduction system in the Beckman LS 8000, and are expressed as a percent specifically bound compared to control.

Benzodiazepine receptors are obtained from male Holstein calves. Immediately after exsanguination, the brains are quickly removed and placed in ice. Dissection of the caudate nucleus is completed within 2 hours after sacrifice and the tissue weighed, and homogenized (1:10, W/V) in 0.05 M Tris buffer (pH 7.1 at 37° C.) using a Brinkmann Polytron for 10 seconds with a rheostat setting of 8. The homogenate is centrifuged for 10 minutes at 20,000 RPM in a Sorvall RC2B centrifuge using a SS 34 head. The supernatant is decanted and the pellet washed twice to remove endogenous dopamine by resuspension with the use of the Brinkmann Polytron and recentrifugation. The final pellet is resuspended in 0.05 M Tris (pH 7.1 at 37° C.) containing 120 mM NaCl, 5 mM KCl, 2 mM $CaCl_2$, and 1 mM $MgCl_2$ in a final concentration of 200 mg wet weight starting material/ml of buffer. The homogenate is stored in 4 ml aliquots in glass bottles in liquid nitrogen.

Substantially similar results are obtainable in a Flunitrazepam Receptor Binding Assay as described by Chang et al., Eur. J. Pharmacol., 48, 213 (1978): when carried out with the non-substantive modifications evident from the following description (hereinafter FBA TEST No. 2): Fresh calf brain cortex is homogenized in a 19 fold volume of Tris-HCl buffer pH 7.4, using a Brinkman Polytron PT 20 and centrifuged at 50'000 g for 0.10 min. The pellets are frozen at −20° C. and resuspended in a 400 fold volume of Tris-buffer pH 7.4 before use for the binding assay. The assay mixtures consist of 1.8 ml of homogenate (corresponding to 4.5 mg of original tissue), 0.1 ml [$^3$H]-Flunitrazepam (final concentration 1.5 nM), and 0.1 ml of buffer for determination of total binding or 0.1 ml of unlabelled Flunitrazepam (final concentration 1 μM) for determination of nonspecific binding, respectively. To assess the potency of various drugs in inhibiting specific binding, drugs are added (instead of buffer) to give 5 to 9 different concentrations between 1 nM and 10 μM, each in duplicate. After incubation for 15 min at 0° C., the assay mixtures are rapidly filtered through Whatman GF/B filters and washed twice with 5 ml of ice cold Tris-buffer. The filters are counted in Rialuma on a LKB Rach-Beta Liquid Scintillation Counter. $IC_{50}$ values (concentration of a test drug which inhibits specific binding of $^3$H-Flunitrazepam by 50%) are determined by linear regression analysis (HILL-Plot).

In other evaluations of benzodiazepine receptors involving the rat brain it is observed that the compounds of the formula I interact in a mode which differs from that of benzodiazepine in two different specific assays as follows:

1. In a Flunitrazepam Receptor Binding Assay as described by Speth et al., above, the compounds of the formula I exhibit—in contrast to classical benzodiazepines—a higher affinity for benzodiazepine receptors in cerebellum compared to hippocampus suggesting a more potent interaction with type I benzodiazepine receptors than with type II benzodiazepine receptors.

2. The compounds of formula I exhibit a differential interaction with benzodiazepine receptors after photoaffinity labelling with flunitrazepam when examined by the method described in Neuroscience Letters, 31 (1982), pages 65–69. In this assay conventional benzodiazepines exhibit after photoaffinity labelling with flunitrazepam when compared to untreated membranes a 20-fold and more increased $IC_{50}$ values after photoaffinity labelling whereas benzodiazepine antagonists exhibit unaltered $IC_{50}$ values. The compounds of formula I exhibit only up to 4-fold increased $IC_{50}$ values after photoaffinity labelling of benzodiazepine receptors when compared to the values obtained with control membranes. In addition, compounds of formula I exhibit increased affinity for benzodiazepine receptors of rat cerebral cortex in presence of 4-aminobutyric acid when compared to their respective affinity in the absence of 4-aminobutyric acid.

The mode of interaction of the compound of the formula I with benzodiazepine receptors therefore differs from that of conventional benzodiazepine and from that of benzodiazepine antagonists. The compounds of formula I possess a relatively high level of activity in the above indicated tests and possess an interesting and desirable spectrum of tranquilizer activity, particularly anti-anxiety activity. In addition, the compounds of formula I are indicated to have a stimulating effect on behavior in observation tests and to lack undesirable CNS depressant effects. For example, the compounds of the formula I are also indicated to be active in the well known hexobarbital reinduction test. However, at the doses at which the compounds are indicated to be useful as minor tranquillizers, e.g. by the FBA test and the conflict segment of the Geller Conflict test, the compounds I are generally indicated to be only weakly active or essentially inactive in a number of other standard CNS depressant tests, such as in sleep studies in monkeys, spinal reflex test in cats, the chemically induced convulsions test (in mice with N-sulfamoyl hexahydrol azepine), the Dunham rotarod test and, of further interest, in the variable interval segment of the Geller Conflict test. The compounds I are therefore indicated to have a very specific and desirable mode of action in effecting tranquillization, and in particular are indicated to effect tranquillization with a substantially reduced sedative action which is associated with, e.g. drowsiness, in most if not all of the currently available tranquilizers.

The compounds of the formula I exhibit a relatively high level of CNS depressant activity in the FBA test and the conflict segment of the Geller Conflict test and hence possess an interesting and desirable spectrum of tranquilizer activity, including particularly anti-anxiety activity. For such use as tranquilizers, particularly in the treatment of anxiety and/or tension, the amount of the compounds of the formula I to be administered will vary depending upon the compound used, mode of administration, the condition being treated, the severity of the condition and other known factors. However, in general satisfactory results are obtained when administered at a daily dosage of from 0.1 to 100 milligrams per kilogram of body weight, preferably given orally and in divided doses 2 to 4 times a day, or in sustained release form. For larger mammals the administration of from 10 to 500 milligrams per day provides satisfactory results and dosage forms for internal administration comprise from 2.5 to 250 milligrams of the compound in admixture with a solid or liquid carrier. The daily dosage for larger mammals is preferably from 10 to 200 milligrams and dosage forms preferably contain from 2.5 to 100 milligrams.

Pharmaceutical compositions provided by the invention and useful for effecting tranquilization of mammals contain a compound of the formula I as active ingredient and one or more conventional pharmaceutically acceptable carriers, including such other conventional adjuvants as may be desired or necessary. Such compositions may be in conventional orally administerable forms such as tablets, capsules, granules, dispersible powders, elixirs, syrups, suspensions and the like or in conventional parenterally administerable forms such as an injectable sterile solution, suspension or the like, e.g., a sterile injectable aqueous suspension. Such compositions including applicable unit dosage forms thereof may be prepared according to any method known in the art for the manufacture of pharmaceutical compositions. The compositions of the invention adapted for oral or parenteral administration may contain from 1% to 90% by total weight of active ingredient in combination with the carrier, more usually 3% to 60%. The preferred unit dosage forms are the essentially solid forms adapted for oral administration.

A representative formulation for administering 3 to 4 times a day or as needed in treatment of anxiety and/or tension is a capsule prepared by conventional capsulating techniques and containing the following ingredients:

| Ingredient | Parts by Weight |
| --- | --- |
| 1-n-butyl-7-trifluoromethyl-2,3-dihydro imidazo[2,1-b]quinazolin-5(1H)-one | 10 |
| Lactose | 200 |

The preferred compounds of the present invention have R° being alkyl of 2 to 5 carbon atoms.

The following examples are for purposes of illustration only.

EXAMPLE 1

1-Ethyl-7-trifluoromethyl-2,3-dihydro-imidazo[2,1-b]quinazolin-5(1H)-one

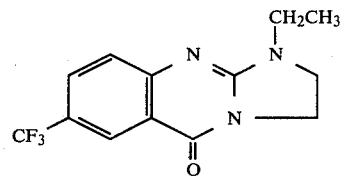

A solution of 3.6 g. of 1-ethyl-2-methylthioimidazoline, 5.0 g. of 2-amino-5-trifluoromethylbenzoic acid and 50 ml. of dimethylacetamide is refluxed for 24 hours and then the reaction mixture concentrated in vacuo. The residue is dissolved in methylene chloride, washed first with 2 N sodium hydroxide solution and then with water, dried over magnesium sulfate, filtered and chromatographed on silica gel while eluding with methylene chloride to obtain 1-ethyl-7-trifluoromethyl-2,3-dihydro-imidazo[2.1-b]quinazolin-5(1H)-one.

EXAMPLE 2

1-n-butyl-7-trifluoromethyl-2,3-dihydro-imidazo[2,1-b]quinazolin-5(1H)-one

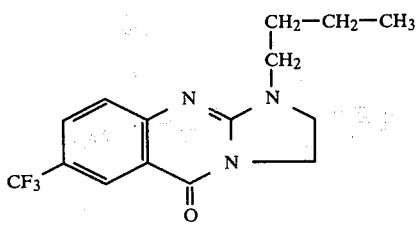

A mixture of 2.0 g. of 7-trifluoromethyl 2,3-dihydro-imidazo[2,1-b]quinazolin-5(1H)-one in 25 ml. dimethylacetamide is treated with 450 mg. of sodium hydride and heated at 50° C. for 3-5 hours. The resulting solution is then treated by addition of 1.6 g. of bromobutane in 10 ml. of dimethylacetamide and stirred for 15 hours at room temperature. The resulting mixture is evaporated to a small volume, dissolved in methylene chloride and water, the organic layer separated, washed with water, dried and evaporated to an oil which is treated with carbon, filtered through Celite and dissolved in hot pentane to crystallize on cooling 1-n-butyl-7-trifluoromethyl-2,3-dihydro-imidazo[2,1-b]quinazolin-5(1H)-one, m.p. 67°-68° C. This compound gives an IC50 of 15 in FBA Test No. 2.

The 7-trifluoromethyl 2,3-dihydro-imidazo[2,1-b]quinazolin-5(1H)-one employed in this Example 2 is obtained analogously to process (a) by reacting 13 g. of a compound III in which R° is hydrogen with 30 g. of the compound II under nitrogen for 20 hours followed by evaporation to a thick oil, treatment with methylene chloride/water, washing of the separated organic layer with water, drying, evaporation, dissolution with methanol, treatment with charcoal, filtering, concentration to a volume of 100 ml. and cooling to crystallize (2 hours with stirring) the 1-trifluoromethyl-2,3-dihydro-imidazo[2,1-b]quinazoline, m.p. 274° C.

What is claimed is:

1. A compound of the formula:

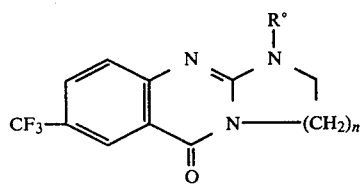

wherein
R° is alkyl of 1 to 8 carbon atoms, and
n is 1 to 2,
or a pharmaceutically acceptable acid addition salt thereof.

2. A compound of claim 1 in which R° is alkyl of 2 to 4 carbon atoms.
3. A compound of claims 1 or 2 in which n is 1.
4. A compound of claims 1 or 2 in which n is 2.
5. A compound of claim 1 in which R° is n-butyl.
6. The compound of claim 5 in which n is 1.
7. The compound of claim 6 in free base form.
8. A pharmaceutical composition comprising an inert pharmaceutically acceptable carrier and a tranquilizing effective amount of claim 1.
9. A composition in accordance with claim 8 in which R° is alkyl of 2 to 5 carbon atoms.
10. A composition in accordance with claims 8 or 9 in which n is 1.
11. A composition in accordance with claims 8 or 9 in which n is 2.
12. A composition in accordance with claim 8 in which R° is n-butyl and n is 1.
13. The method of tranquilizing a mammal comprising administering to a mammal a tranquilizing effective amount of a compound of claim 1.
14. The method of claim 13 in which R° is alkyl of 2 to 5 carbon atoms.
15. The method of claims 13 or 14 in which n is 1.
16. The method of claims 13 or 14 in which n is 2.
17. The method of claim 14 in which R° is n-butyl.
18. The method of claim 17 in which n is 1.
19. The method of claims 13, 14, 17 or 18 in which anxiety and/or tension is reduced upon the daily administration of from 10 to 200 milligrams.

* * * * *